United States Patent
Hoffmann et al.

(10) Patent No.: US 6,554,860 B2
(45) Date of Patent: *Apr. 29, 2003

(54) FOLDABLE IRIS FIXATED INTRAOCULAR LENSES

(75) Inventors: Laurent G. Hoffmann, Foothill Ranch, CA (US); Charles J. Hagemeier, Laguna Beach, CA (US); Wilson Hsing, Santa Ana, CA (US); Donald C. Stenger, Anaheim Hills, CA (US); Eric T. Wilde, Rancho Cucamonga, CA (US)

(73) Assignee: Bausch & Lomb Incorporated, Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/570,721

(22) Filed: May 15, 2000

(65) Prior Publication Data

US 2002/0193877 A1 Dec. 19, 2002

(51) Int. Cl.⁷ .................................................. A61F 2/16
(52) U.S. Cl. ..................................... 623/6.43; 623/6.47
(58) Field of Search ............................... 623/6.38–6.55, 623/6.36

(56) References Cited

U.S. PATENT DOCUMENTS

| 4,298,996 | A | * | 11/1981 | Barnet | 3/13 |
| 5,928,282 | A | * | 7/1999 | Nigam | 623/6 |
| 6,152,959 | A | * | 11/2000 | Portney | 623/6.51 |
| 6,228,115 | B1 | * | 5/2001 | Hoffmann et al. | 623/6.49 |

* cited by examiner

Primary Examiner—David H. Willse
Assistant Examiner—Javier G. Blanco
(74) Attorney, Agent, or Firm—Katherine McGuire; Rita D. Vacca

(57) ABSTRACT

A refractive anterior chamber iris fixated intraocular lens including an optic portion having an outer peripheral edge and two or more but preferably two, three or four balanced haptic elements. Each haptic element is of a relatively narrow arch-like form. Each haptic element is also manufactured to have an inner portion and an outer portion for supporting the optic portion in a patient's eye. The inner portion of each haptic element is permanently connected to the outer peripheral edge of the optic portion. Each haptic element also includes a fixation clamp on the outer portion thereof and a central portion located between the outer portion and the inner portion.

20 Claims, 6 Drawing Sheets

FOLDABLE IRIS FIXATED INTRAOCULAR LENSES

FIELD OF THE INVENTION

The present invention relates to intraocular lenses (IOLs) and a method for making and using the same. More particularly, the present invention relates to anterior chamber iris fixated IOLs designed primarily for refractive correction in phakic eyes where the eye's natural lens remains intact.

BACKGROUND OF THE INVENTION

Visual acuity deficiencies such as myopia (nearsightedness), hyperopia (farsightedness), presbyopia (age-related farsightedness), aphakia (absence of the crystalline lens of the eye) and astigmatism (irregular conformation of the cornea of the eye) are typically corrected through the use of refractive lenses such as spectacles or contact lenses. Although these types of lenses are effective in correcting a wearer's eyesight, many wearers consider the lenses inconvenient. The lenses must be located, worn at certain times, removed periodically and may be lost or misplaced. The lenses may also be dangerous or cumbersome if the wearer participates in athletic activities or suffers an impact in an area near the eyes.

The use of surgically implanted anterior chamber IOLs as a permanent form of refractive correction has been gaining in popularity. IOL implants have been used for years in the anterior or posterior chamber of aphakic eyes as replacements for diseased natural crystalline lenses that have been surgically removed from the eyes. Many different IOL designs have been developed over past years and proven successful for use in aphakic eyes. The successful IOL designs to date primarily include an optic portion with supports therefor, called haptics, connected to and surrounding at least part of the optic portion. The haptic portions of an IOL are designed to support the optic portion of the IOL in the lens capsule, anterior chamber or posterior chamber of an eye once implanted.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than that of the diameter of the inflexible IOL optic portion. Accordingly, more rigid IOLs have become less popular in the market since larger incisions have been found to be associated with an increased incidence of postoperative complications, such as induced astigmatism.

After IOL implantation, both softer and more rigid IOLs positioned within the angle of the anterior chamber of the eye are subject to compressive forces exerted on the outer edges thereof, which typically occur when an individual squints or rubs the eye. Such compressive forces on angle positioned IOLs in either aphakic or phakic eyes may result in tissue damage, decentration of the IOL and/or distortion of the visual image. Compressive forces exerted on an angle positioned IOL may also tend to cause movement of the IOL haptics and axial displacement of the IOL along the optical axis of an eye. Haptic movement and broad haptic contact in the angle of the anterior chamber of an eye has the potential to cause damage to delicate structures within the eye such as the peripheral corneal endothelium, the trabecular meshwork and/or the iris. Movement of an IOL along the optical axis of an eye has the potential to cause the IOL to contact and damage the delicate corneal endothelial cell layer of the eye. Also, angle positioned IOLs of current designs, whether formed of either softer or more rigid materials, tend to deflect along the optical axis of an eye when the haptics are compressed. IOL manufacturers provide a wide range of IOL sizes to more precisely fit IOLs to each particular patient's eye size. Providing a wide range of IOL sizes is an attempt to minimize the potential for haptic compression and the associated axial displacement of the IOL optic along the optical axis of an eye.

Because of the noted shortcomings of current IOL designs, there is a need for aphakic and phakic anterior chamber IOLs designed to eliminate haptic contact and movement in the angle of the anterior chamber and eliminate axial displacement of the IOL optic portion along the optical axis of the eye when compressive forces are exerted against the outer edges thereof. By eliminating an IOL's haptic and optic movement within the angle and anterior chamber respectively, more certain refractive correction may be achieved and the risk of delicate tissue damage may be reduced.

SUMMARY OF THE INVENTION

An anterior chamber iris fixated intraocular lens (IOL) made in accordance with the present invention has an optic portion with an outer peripheral edge and two or more but preferably two, three or four haptic elements for supporting the optic portion in a patient's aphakic or phakic eye. Two, three or four haptic elements are preferred in the present invention to provide a balance between IOL stability and minimized points of fixation on the iris. A lens having two haptic elements is balanced or stabilized by having one haptic element formed on one edge of the optic portion and the second haptic element formed on an opposite edge of the optic portion. A lens having three haptic elements is balanced or stabilized by having two spaced haptic elements formed on one edge of the optic portion and the third haptic element formed on an opposite edge of the optic portion or alternatively by having each of the three haptic elements equally spaced around the periphery of the optic portion. A lens having four haptic elements is balanced or stabilized by having two spaced haptic elements formed on one edge of the optic portion and two spaced haptic elements formed on an opposite edge of the optic portion or alternatively by having each of the four haptic elements equally spaced around the periphery of the optic portion. Each of the haptic elements is preferably of a relatively narrow arch-like form designed to allow the IOL to be easily folded for insertion thereof through a relatively small incision within the eye.

Each haptic element is designed in the form of a relatively narrow arch with a fixation clamp preferably at the center or peak thereof for ease in fixating the same on the anterior surface of the iris of an eye. Each of the haptic elements also has an inner portion and an outer portion with the inner portion being connected to the outer peripheral edge of the optic portion. Each haptic element includes two interlocking smooth, serrated or toothed edges on the outer portion thereof to form a fixation clamp. The fixation clamps are designed to secure the IOL within the anterior chamber of an eye by engaging the relatively non-mobile outer peripheral edge of the iris of an eye.

Accordingly, it is an object of the present invention to provide intraocular lenses for use in aphakic and phakic eyes.

Another object of the present invention is to provide intraocular lenses for use in aphakic and phakic eyes, which eliminate anterior chamber angle contact.

Another object of the present invention is to provide intraocular lenses for use in aphakic and phakic eyes, which minimize axial displacement of the optic portions of the lenses along the optical axis of the eyes.

Another object of the present invention is to provide intraocular lenses that allow for increased ease of implantation thereof.

Another object of the present invention is to provide intraocular lenses for use in aphakic and phakic eyes, which minimize damage to tissues in the interior of the eyes.

Still another object of the present invention is to provide intraocular lenses, which are resistant to decentration within the eyes.

These and other objectives and advantages of the present invention, some of which are specifically described and others that are not, will become apparent from the detailed description, drawings and claims that follow, wherein like features are designated by like numerals.

DETAILED DESCRIPTION OF THE INVENTION

Figure 1:
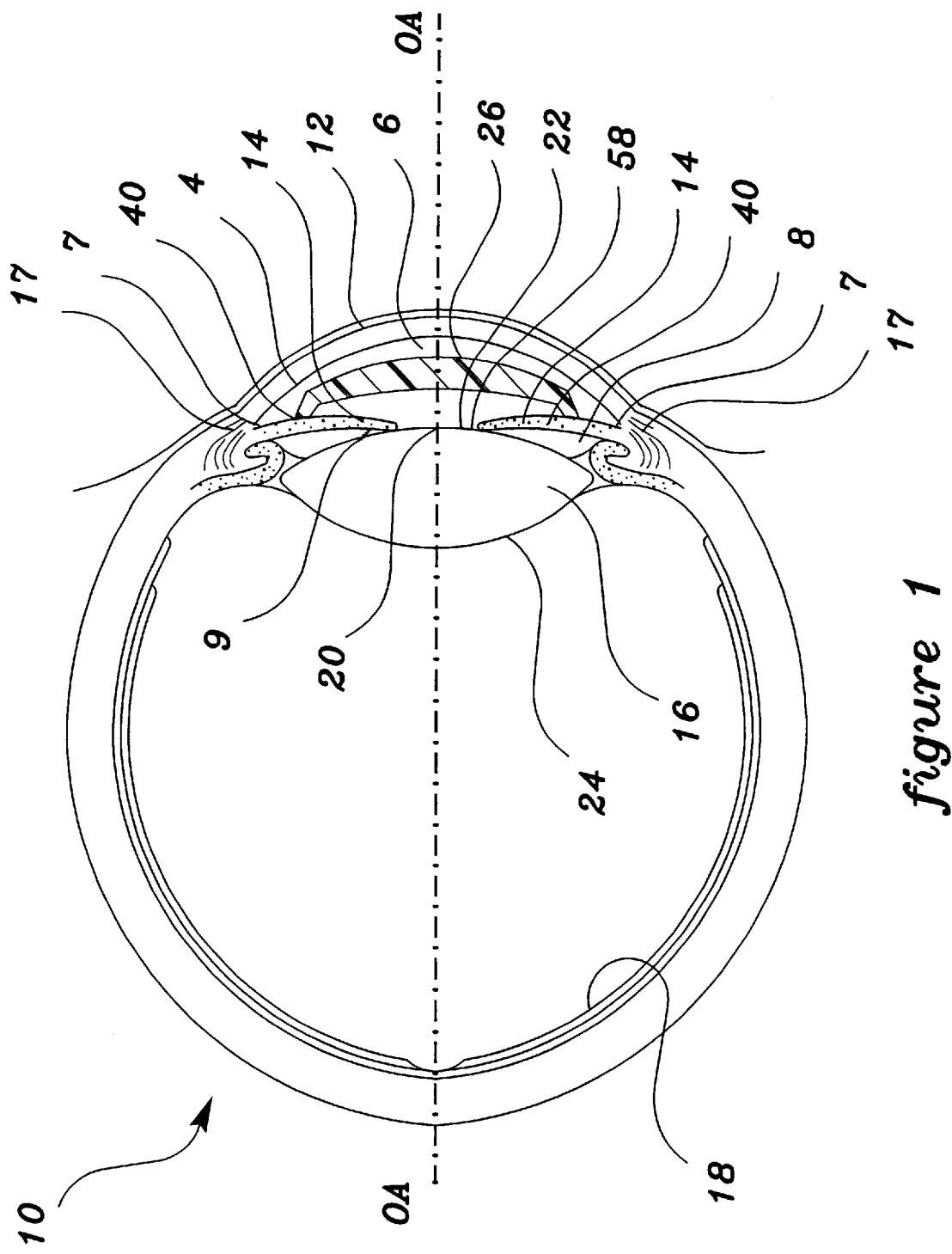
FIG. 1 is a schematic representation of the interior of a phakic human eye including a natural lens and a refractive IOL implanted in the anterior chamber of the eye.

FIG. 1 illustrates a simplified diagram of an eye 10 showing landmark structures relevant to the implantation of an intraocular lens of the present invention. Eye 10 includes an optically clear cornea 12 and an iris 14 with a relatively non-mobile peripheral edge 40. A natural crystalline lens 16 and a retina 18 are located behind iris 14 of eye 10. Eye 10 also includes anterior chamber 6 with angle 7 located in front of iris 14 and a posterior chamber 8 located between iris 14 and natural lens 16. An IOL 26, such as that of the present invention, is preferably implanted in anterior chamber 6 to correct refractive errors while healthy natural lens 16 remains in place (phakic application). However, IOL 26 likewise may be implanted in anterior chamber 6 of aphakic eyes where the natural lens 16 has been removed. Eye 10 also includes an optical axis OA—OA that is an imaginary line that passes through the optical center 20 of anterior surface 22 and posterior surface 24 of lens 16. Optical axis OA—OA in the human eye 10 is generally perpendicular to a portion of cornea 12, natural lens 16 and retina 18.

Figure 2:
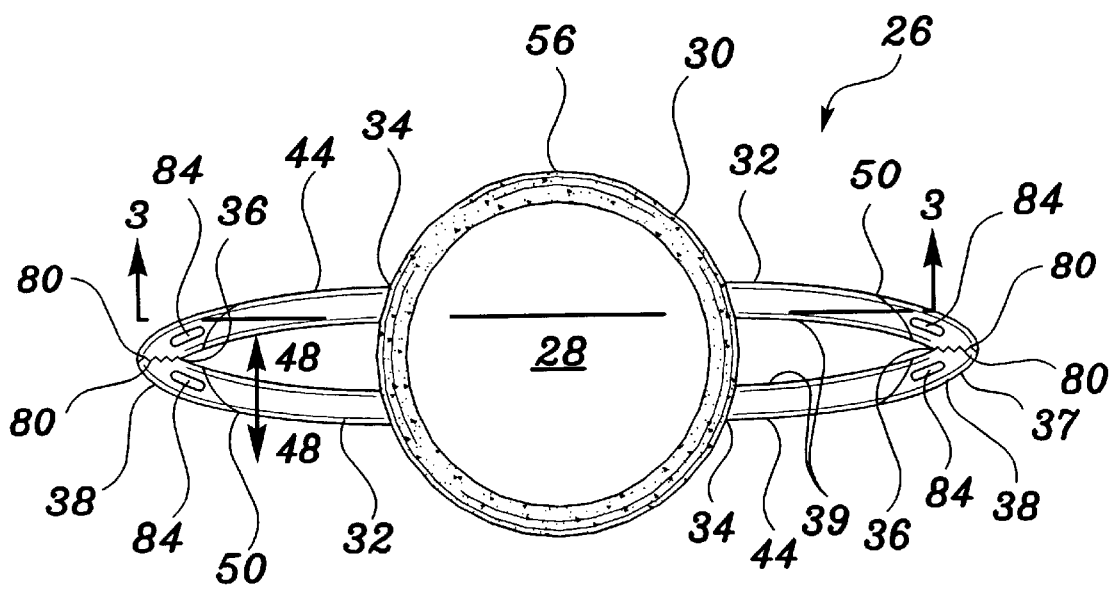
FIG. 2 is a plan view of an IOL with two haptics made in accordance with the present invention.
Figure 5:
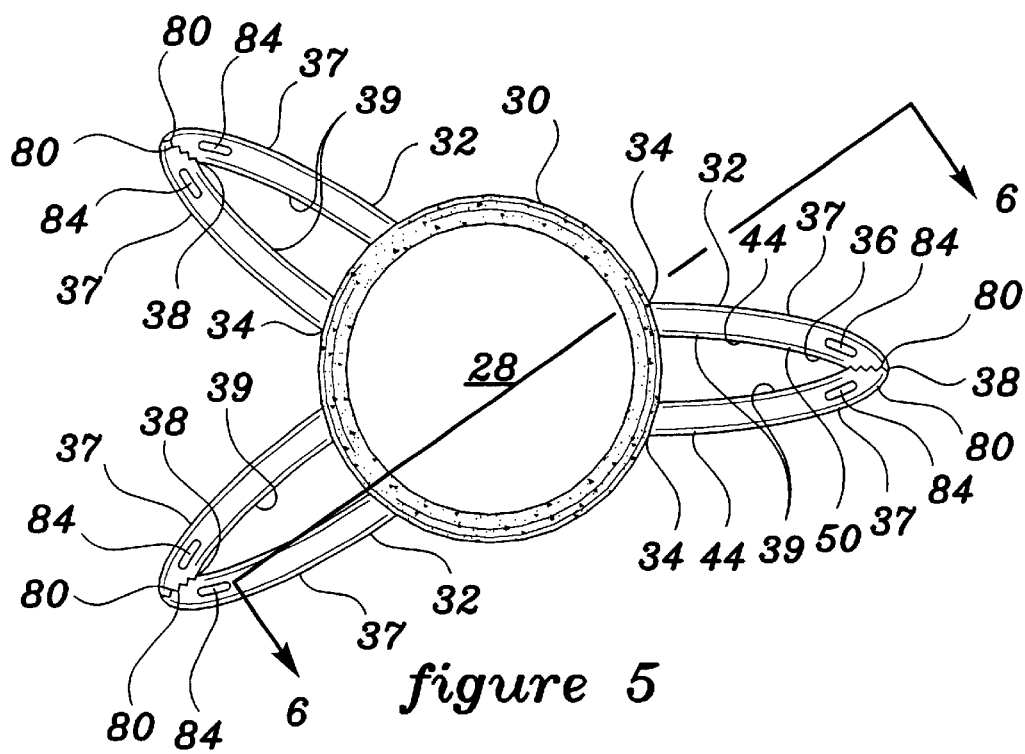
FIG. 5 is a plan view of an IOL with three haptics made in accordance with the present invention.
Figure 8:
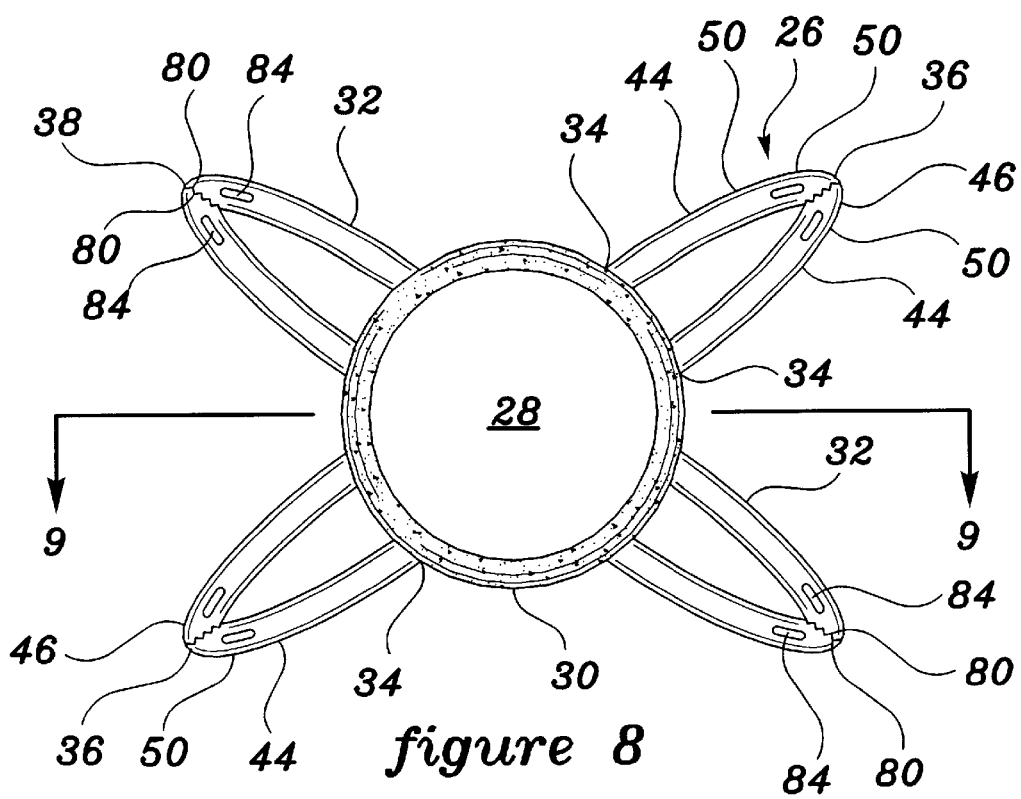
FIG. 8 is a plan view of an IOL with four haptics made in accordance with the present invention.

The IOL of the present invention, as best illustrated in FIGS. 2, 5 and 8 identified by reference numeral 26, is designed for implantation in anterior chamber 6 of a patient's eye 10. IOL 26 has an optic portion 28 with an outer peripheral edge 30. Preferably integrally formed on peripheral edge 30 of optic portion 28 are two or more but preferably two, three or four separate looped or arch-like haptic elements 32. Each haptic element 32 is manufactured to have an inner portion 34 and an outer portion 36. Inner portions 34 of haptic elements 32 are preferably integrally formed with and permanently connected to outer peripheral edge 30 of optic portion 28. Alternatively however, inner portions 34 of haptic elements 32 may be attached to optic portion 28 by staking, chemical polymerization or other methods known to those skilled in the art. Each haptic element 32 also includes at outer portion 36, a fixation clamp 38 in the center or peak 46 thereof designed to engage relatively non-mobile outer peripheral edge 40 of iris 14 in anterior chamber 6. In accordance with the present invention, IOL 26 is held in proper position in anterior chamber 6 through constant compressive forces exerted by fixation clamps 38 on relatively non-mobile outer peripheral edge 40 of iris 14. Iris fixation of IOL 26 is desired to avoid haptic element 32 contact and damage to delicate tissues within angle 7 of eye 10.

Figure 3:
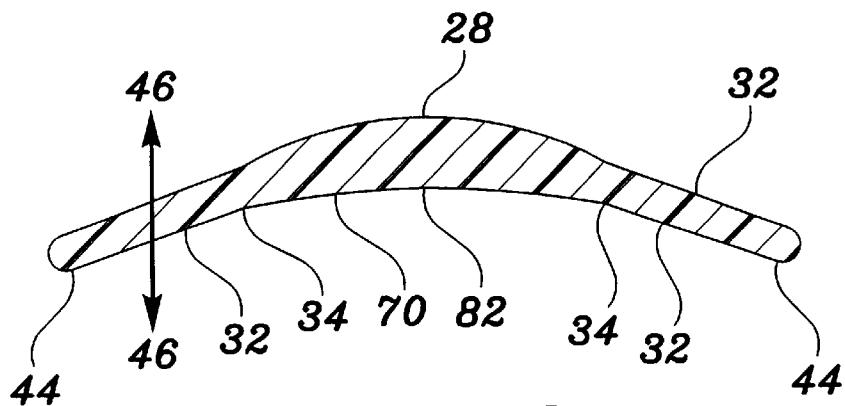
FIG. 3 is a side cross sectional view of the IOL of FIG. 2 taken along line 3—3.
Figure 4:
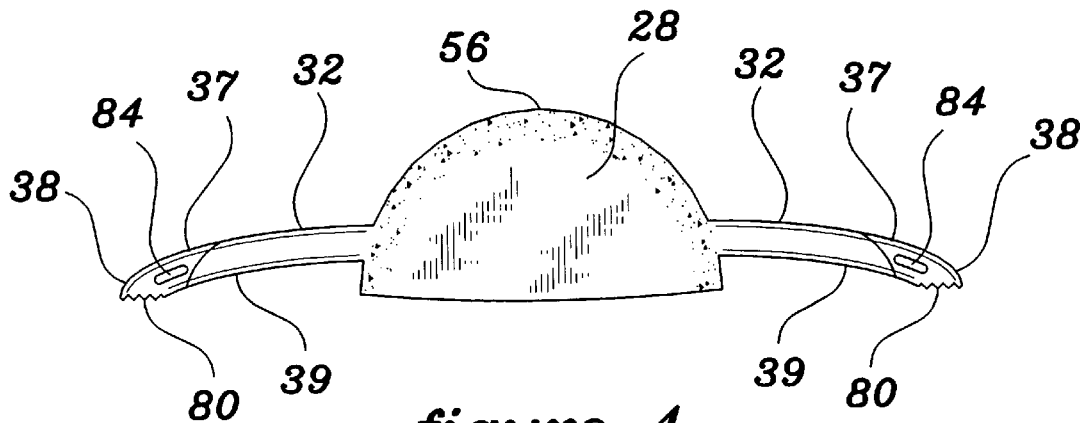
FIG. 4 is a plan view of the IOL of FIG. 2 in a folded state.
Figure 6:
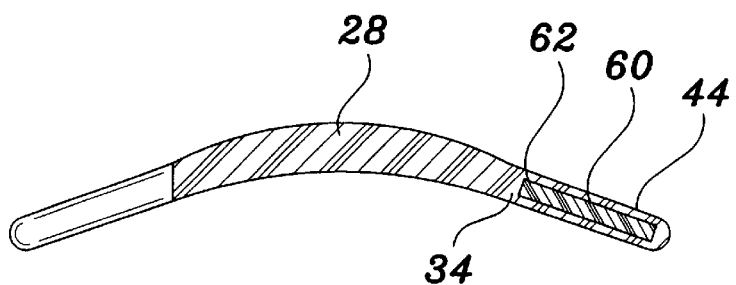
FIG. 6 is a side cross sectional view of the IOL of FIG. 5 taken along line 6—6.
Figure 7:
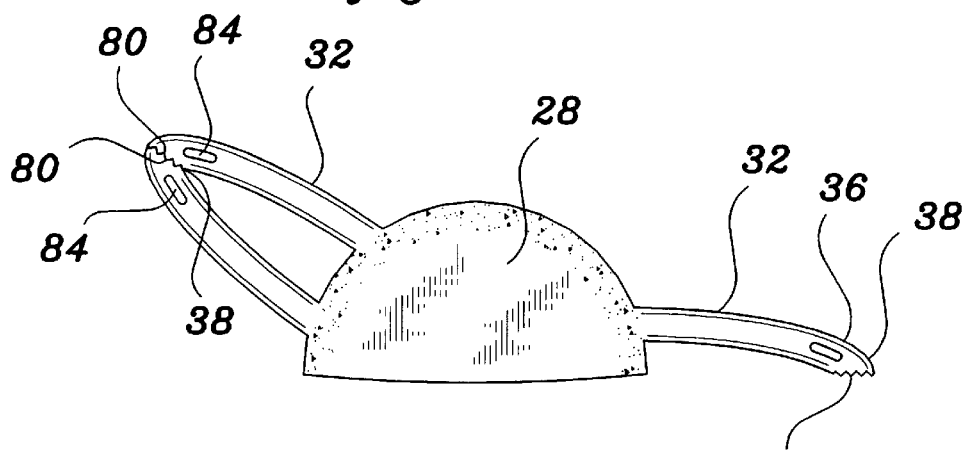
FIG. 7 is a plan view of the IOL of FIG. 5 in a folded state.
Figure 9:
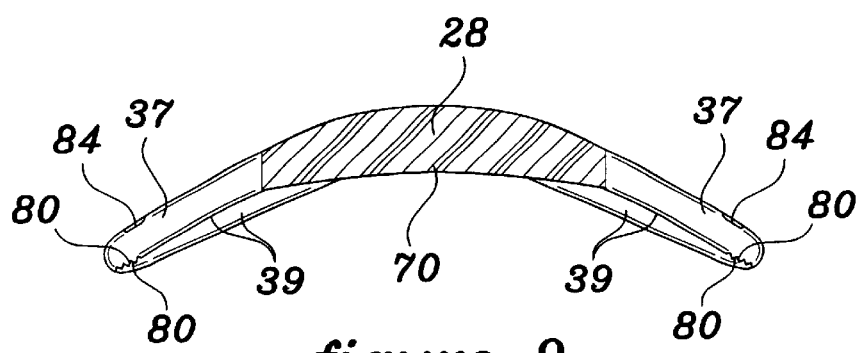
FIG. 9 is a side cross sectional view of the IOL of FIG. 8 taken along line 8—8.
Figure 10:
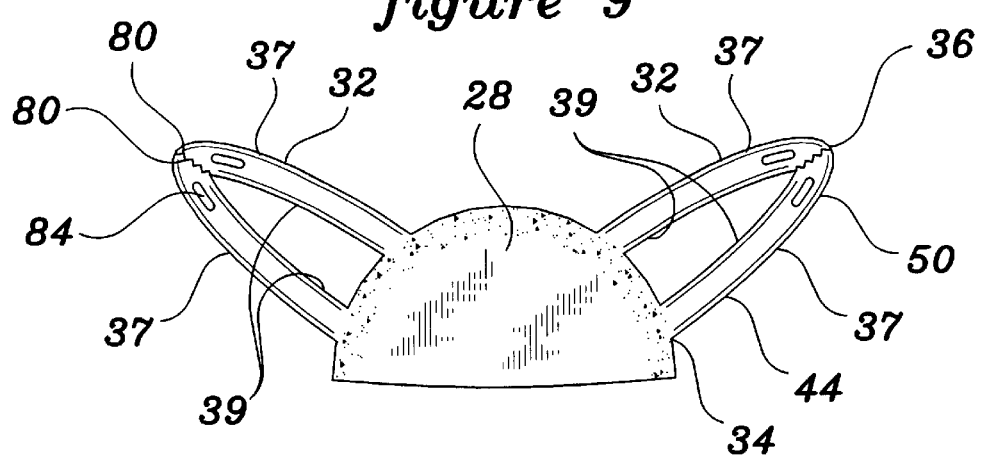
FIG. 10 is a plan view of the IOL of FIG. 8 in a folded state.
Figure 11:
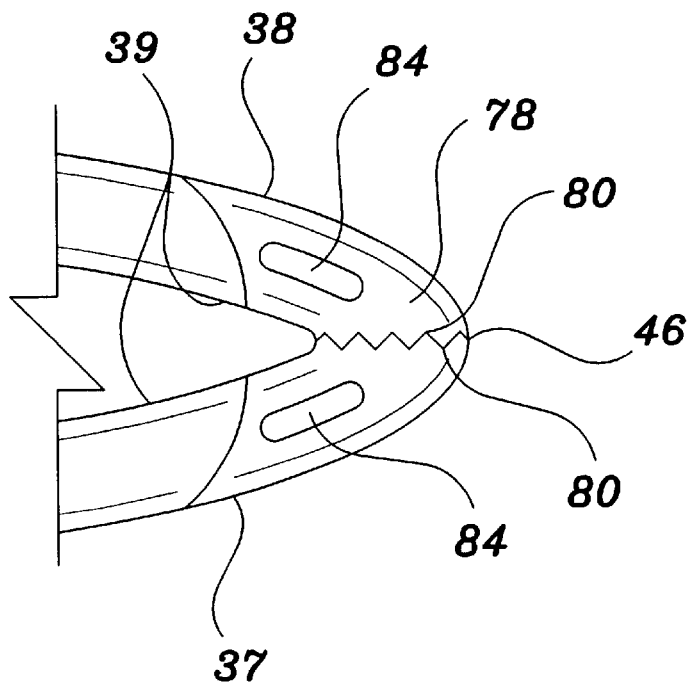
FIG. 11 is an enlarged plan view of the fixation clamp of the IOL of FIG. 2.
Figure 12:
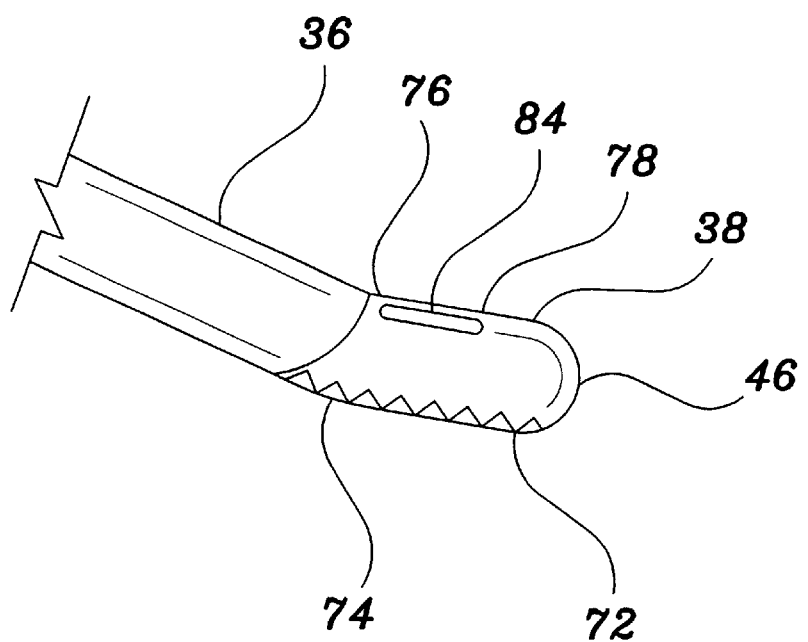
FIG. 12 is an enlarged side view of the fixation clamp of FIG. 11.

The required functional characteristics of haptic elements 32 to maintain adequate compressive forces on iris 14, are achieved through the unique design thereof. IOL 26 has relatively narrow arch-like haptic elements 32 formed with a central portion 44 adjacent to inner portion 34 permanently connected to outer peripheral edge 30 of optic portion 28. Central portion 44 has a dimension in plane 46—46, best illustrated in FIGS. 3, 6 and 9, generally parallel to optical axis OA—OA, approximately equal but preferably less than that of plane 48—48, best illustrated in FIGS. 2, 5 and 8, generally perpendicular to optical axis OA—OA. Each half of haptic element 32 is resistant to being deflected or flexed in a direction away from its other half due to each half being biased toward one another in an arch-like design. A transition portion 50, of significantly decreasing size in dimension in plane 46—46 extends from central portion 44 to fixation clamp 38. Fixation clamps 38 include two interlocking smooth, serrated or toothed edges 80 as illustrated in FIGS. 11 and 12. Smooth, serrated or toothed edges 80 of fixation clamps 38 separate if necessary upon folding IOL 26 as illustrated in FIGS. 4, 7 and 10. This allows IOL 26 to be implanted in an eye 10 through a relatively small incision, such as less than 4.0 mm using surgical forceps or an inserter as known to those skilled in the art. The outer portions 36 which support fixation clamps 38 may optionally be slightly bowed to form a slightly convex surface 72 on the posterior surface 74 and a slightly concave surface 76 on the anterior surface 78 of fixation clamps 38. Fixation clamps 38 are optionally slightly bowed for ease of fixation on relatively non-mobile peripheral edge 40 of iris 14.

The subject IOL 26 is preferably produced having an optic portion 28 approximately 4.5 to 9.0 mm, but preferably approximately 5.0 to 6.0 mm and most preferably 5.5 mm in diameter and approximately 0.5 mm to 1.0 mm, but preferably approximately 0.6 to 0.8 mm and most preferably 0.7 mm in thickness at peripheral edge 30. Haptic elements 32 extend in a relatively narrow arch-like configuration for ease of implantation through a relatively small surgical incision and increase or decrease in length depending upon the diameter of optic portion 28. As the diameter of optic portion 28 increases, the length of haptic elements 32 decrease. Likewise, as the diameter of optic portion 28 decreases, the length of haptic elements 32 increase. In general, haptic elements 32 are formed to be approximately 2.6 to 6.0 mm, but preferably approximately 3.4 to 5.0 mm and most preferably approximately 4.2 mm in length measuring the cord of the arc from the center of inner portion 34 to the center of its corresponding inner portion 34. The overall diameter of IOL 26 is approximately 6.0 to 10.0 mm, but preferably approximately 7.0 to 9.0 mm and most preferably approximately 8.0 mm. Haptic elements 32 on IOL 26 preferably have vaulted arch-like configurations as illustrated in FIGS. 3, 6 and 9 to allow appropriate fixation to relatively non-mobile peripheral edge 40 of iris 14 while avoiding contact between the posterior surface 70 of optic portion 28 and the mobile portions 9 of iris 14. A vault of approximately 0.5 to 1.0 mm is preferred for central placement of IOL 26 between iris 14 and corneal endothelium 4. Central portion 44 of haptic element 32 is approximately 0.5 to 2.5 mm, but preferably approximately 1.0 to 2.0 mm and most preferably 1.6 mm in length; approximately 0.2 to 0.8 mm, but preferably approximately 0.2 to 0.6 mm and most preferably approximately 0.3 mm in thickness in plane 46—46 and approximately 0.2 to 1.0 mm, but preferably approximately 0.3 to 0.7 mm and most preferably approximately 0.46 mm in width in plane 48—48. Transition portion 50 is approximately 0.4 to 1.1 mm, but preferably approximately 0.5 to 1.0 mm and most preferably approximately 0.8 mm in length. Fixation clamps 38 are approximately 0.2 to 1.0 mm, but preferably approximately 0.4 to 0.6 mm and most preferably approximately 0.5 mm in length and approximately 0.03 to 0.3 mm, but preferably approximately 0.1 to 0.2 mm and most preferably approximately 0.15 mm in thickness in plane 46—46 and approximately 0.05 to 0.5 mm, but preferably approximately 0.1 to 0.4 mm and most preferably approximately 0.3 mm in width in plane 48—48. Fixation clamps 38 illustrated in FIGS. 11 and 12 are two relatively small interlocking smooth, serrated or toothed edges 80 designed for secure fixation of IOL 26 to relatively non-mobile peripheral edge 40 of iris 14.

Figure 13:
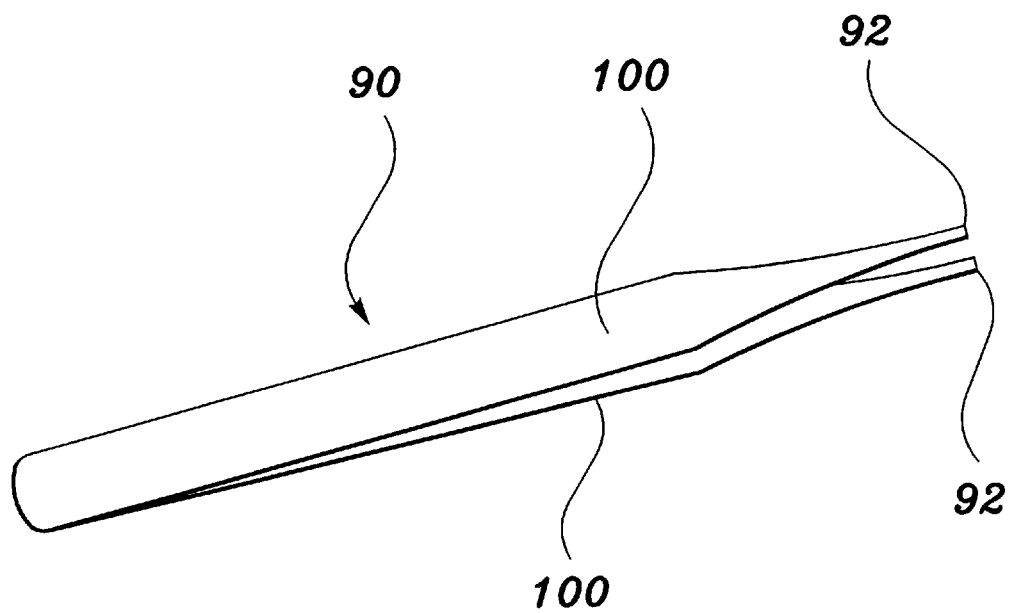
FIG. 13 is a perspective view of surgical forceps.
Figure 14:
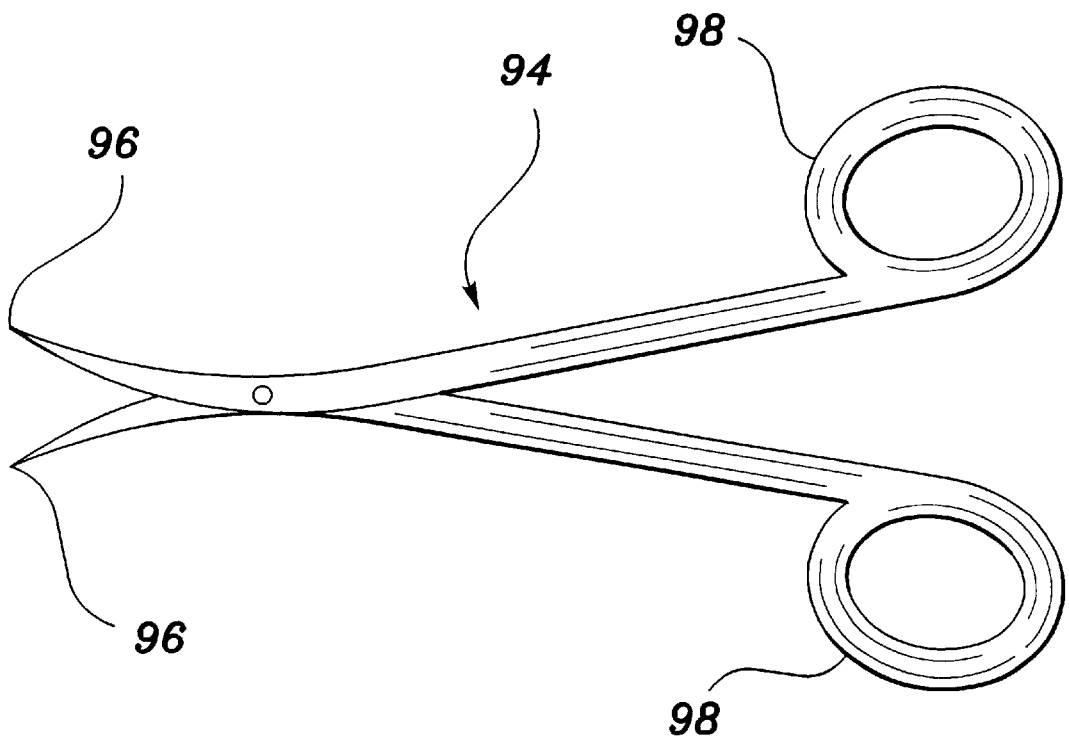
FIG. 14 is a perspective view of surgical retractors.

As provided through the dimensions of IOL 26 above, haptic elements 32 gradually change from being relatively thin in plane 46—46 at outer portion 36 to being relatively thick at inner portion 34 and optic portion 28, with central portion 44 exhibiting a dimension in plane 46—46 that is near equal but preferably less than that of the width in plane 48—48 to achieve a low profile. Fixation clamps 38 of haptic elements 32 are designed to maintain a constant compression force to reliably pinch and/or pierce relatively non-mobile peripheral edge 40 of iris 14 for proper fixation of IOL 26. Fixation clamps 38 may be fixated on relatively non-mobile peripheral edge 40 with the use of common surgical forceps 90 or retractor 94. If IOL 26 is manufactured with a planar or more preferably a bowed fixation clamp 38 as described above, two spaced free tips 92 of common surgical forceps 90 as illustrated in FIG. 13 are placed in the two spaced indentations 84 on fixation clamp 38. Handles 100 of surgical forceps 90 are then compressed in an attempt to bring free tips 92 into closer proximity to one another. The compressive forces from free tips 92 on indentations 84 serve to open the two interlocking smooth, serrated or toothed edges 80 of fixation clamp 38. Alternatively, the need to incorporate or to use spaced indentations 84 may be eliminated by placing two spaced free tips 92 of surgical forceps 90 on exterior edges 37 of outer portion 36 and compressing the same in an attempt to bring free tips 92 into closer proximity to one another. The compressive forces from free tips 92 on exterior edges 37 serve to open the two interlocking smooth, serrated or toothed edges 80 of fixation clamps 38. The open smooth, serrated or toothed edges 80 are then placed on relatively non-mobile peripheral edge 40 of iris 14. Once positioned on iris 14 as described, compressive forces are released from spaced free tips 92 of surgical forceps 90. The smooth, serrated or toothed edges 80 of fixation clamp 38 thereby close pinching and/or piercing relatively non-mobile peripheral edge 40 of iris 14. Alternatively, IOL 26 may be positioned on iris 14 by placing two free tips 96 of retractor 94 as illustrated in FIG. 14 in the two spaced indentations 84 on fixation clamp 38. The handles 98 of retractor 94 are compressed in an attempt to spread apart free tips 96. The outwardly applied forces from free tips 96 on indentations 84 serve to open the two interlocking smooth, serrated or toothed edges 80 of fixation clamp 38. Alternatively, the need to incorporate or to use spaced indentations 84 may be eliminated by placing free tips 96 of surgical retractor 94 within interior edges 39 of outer portion 36 and compressing handles 98 to spread apart free tips 96. The forces from free tips 96 on interior edges 37 serve to open the two interlocking smooth, serrated or toothed edges 80 of fixation clamps 38. The open smooth, serrated or toothed edges 80 are then placed on relatively non-mobile peripheral edge 40 of iris 14. Once positioned on iris 14 as described, outwardly applied forces are released from free tips 96 of retractor 94. The smooth, serrated or toothed edges 80 of fixation clamp 38 thereby close pinching and/or piercing relatively non-mobile peripheral edge 40 of iris 14. When the subject anterior chamber iris fixated IOL 26 is used as a refractive lens, a stable, reliable refractive correction is provided with minimal damage to delicate tissues within the eye.

The desired functional characteristics of IOL 26 may likewise be achieved or enhanced by incorporating a stiffening element 60, in the shape of a ribbon, in one or more haptic elements 32, as illustrated in FIG. 6. Stiffening element 60 may be positioned in haptic element 32 so that flat face 62 is oriented parallel to the dimension 48—48. Stiffening element 60 functions in a manner similar to that of an I-beam in construction to prevent inadvertent opening of fixation clamps 38.

Stiffening element 60 is formed of a less flexible material than that of IOL 26. Suitable materials for stiffening element 60 include but are not limited to polyimides, polyolefins, high-density polyethylenes, polyesters, nylons, metals or any biocompatible material with suitable stiffening characteristics. Stiffening element 60 may be used in conjunction with haptic elements 32 described above or in cases where a thinner haptic design is desired while still achieving the desired functional characteristics.

Suitable materials for the production of the subject IOL 26 include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. It is preferred that IOL 26 be of a bicomposite material design whereby optic 28 and haptic elements 32 with the exception of fixation clamps 38 are manufactured from a compressible or foldable material such as but not limited to a silicone or hydrogel material such as but not limited to 2-hydroxyethyl methacrylate (HEMA) and 6-hydroxyhexyl methacrylate (HOHEXMA), i.e., poly(HEMA-co-HOHEXMA). In such a case, fixation clamps 38 are manufactured from a relatively more rigid material such as but not limited to a relatively more rigid hydrogel, polymethylmethacrylate (PMMA) or a polyimide as illustrated in FIGS. 2, 4, 11 and 12 and described in U.S. Pat. Nos. 5,217,491 and 5,326,506, each incorporated herein in its entirety by reference. Alternatively, optic 28 may be manufactured from a compressible or foldable material such as but not limited to a silicone or hydrogel material, and haptics 32 and fixation clamps 38 may be manufactured from a relatively more rigid material such as but not limited to a relatively more rigid hydrogel, PMMA or polyimide. Poly(HEMA-co-HOHEXMA) is the preferred material for the manufacture of the optic portion 28 of IOL 26 due to its equilibrium water content of approximately 18 percent by weight, and high refractive index of approximately 1.474, which is greater than that of the aqueous humor of the eye, i.e., 1.33. A high refractive index is a desirable feature in the production of IOLs to impart high optical power with a minimum of optic thickness. By using a material with a high refractive index, visual acuity deficiencies may be corrected using a thinner IOL. A thin IOL, such as that of IOL 26, is particularly desirable in phakic applications to minimize potentially harmful contact between the IOL 26 and the iris 14 and/or the corneal endothelium 4. Poly(HEMA-co-HOHEXMA) is also a desirable material in the production of IOLs 26 due to its mechanical strength, which is suitable to withstand considerable physical manipulation. Poly(HEMA-co-HOHEXMA) also has desirable memory properties suitable for IOL 26 use. IOLs 26 manufactured from a material possessing good memory properties such as those of poly (HEMA-co-HOHEXMA) unfold in a controlled manner in an eye 10, rather than explosively, to its predetermined shape. Explosive unfolding of IOLs 26 is undesirable due to potential damage to delicate tissues within the eye 10. Poly(HEMA-co-HOHEXMA) also has dimensional stability in the eye 10.

Although the teachings of the present invention are preferably applied to soft or foldable IOLs 26 formed of a foldable or compressible material, the same may also be applied to harder, less flexible lenses formed of a relatively rigid material such as PMMA having flexible haptics formed either of the same or a different material.

Optic portion 28 of IOL 26 can be a positive powered lens from 0 to approximately +40 diopters or a negative powered lens from 0 to approximately −30 diopters. Optic portion 28 may be biconvex, piano-convex, piano-concave, biconcave or concave-convex (meniscus), depending upon the power required to achieve the appropriate central and peripheral thickness for efficient handling.

Optic portion 28 of the subject IOL 26 may optionally be formed with a glare reduction zone 56 of approximately 0.25 to 0.75 mm but more preferably approximately 0.3 to 0.6 mm and most preferably 0.5 mm in width adjacent outer peripheral edge 30 for reducing glare when outer peripheral edge 30 of IOL 26 is struck by light entering eye 10 during high light or at other times when pupil 58 is dilated. Glare reduction zone 56 is typically fabricated of the same material as optic portion 28, but may be opaque, roughened, textured, colored or patterned in a conventional manner to block or diffuse light in plane with optical axis OA—OA.

Subject IOL 26 may be molded using a removable mold as known to those skilled in the art or may be manufactured by first producing discs from a material of choice as described in U.S. Pat. Nos. 5,217,491 and 5,326,506 each incorporated herein in its entirety by reference. IOL 26 may then be machined from the material discs in a conventional manner. Once machined, IOL 26 may be polished, cleaned, sterilized and packaged by a conventional method known to those skilled in the art.

The subject IOL 26 is used in eye 10 by creating an incision in cornea 12, inserting IOL 26 in anterior chamber 6, pinching and/or piercing relatively non-mobile peripheral edge 40 with fixation clamps 38 and closing the incision in accordance with methods known to those skilled in the art.

IOL 26 of the present invention provides for a refractive lens suitable for use in anterior chamber 6 of eye 10. IOL 26 has haptic elements 32 with functional characteristics that minimize or eliminate axial displacement along optical axis OA—OA of eye 10 and lens contact in the angle 7 of anterior chamber 6 thereby preventing damage to delicate eye tissues such as the trabecular meshwork 17 and the corneal endothelium 4. IOL 26, having the specific functional characteristics described herein is also advantageous because one or a few lens sizes suitably fit eyes 10 of most sizes since position of attachment to iris 14 may be varied slightly. By providing a "universal" lens such as that of the present invention, clinical risks to patients due to improperly sized lenses for angle 7 are minimized. Likewise, manufacturers' need to produce IOLs of many sizes to fit eyes of many sizes is eliminated, thus reducing production and inventory costs associated therewith. Ophthalmologists also benefit from subject IOL 26 in that time is saved by eliminating the need to determine each patient's particular eye size and costs associated with maintaining large inventories of varying sized lenses.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

We claim:

1. An anterior chamber iris fixated intraocular lens to be implanted within an eye generally perpendicular to the eye's optical axis comprising:

an outer peripheral edge defining an optic portion, two or more arch-like haptic elements permanently connected to the outer peripheral edge, each continuously decreasing in thickness in a plane parallel to the eye's optical axis moving in a direction away from the outer peripheral edge to an outermost peak thereof, and an iris fixation clamp formed in said outermost peak of each arch-like haptic element, capable of separating upon folding of said intraocular lens, to allow for folded implantation of said intraocular lens through a relatively small incision.

2. The intraocular lens of claim 1 wherein the haptic elements and the optic portion are both formed of a foldable or compressible material.

3. The intraocular lens of claim 1 wherein at least a portion of the haptic elements and the optic portion are formed from differing materials.

4. The intraocular lens of claim 1 wherein the haptic elements, the fixation clamps and the optic portion are formed from differing materials.

5. The intraocular lens of claim 1 wherein the fixation clamps are formed from a material relatively more rigid than that of the optic portion.

6. The intraocular lens of claim 1 wherein the fixation clamps are formed from a material relatively more rigid than that of the haptic elements.

7. The intraocular lens of claim 1 wherein said lens optic portion is formed from a material selected from the group consisting of silicone polymers, hydrocarbon and fluorocarbon polymers, hydrogels, soft acrylic polymers, polyester, polyamides, polyurethane, silicone polymers with hydrophilic monomer units, fluorine-containing polysiloxane elastomers and combinations thereof.

8. The intraocular lens of claim 1 wherein said lens optic portion is formed from a hydrogel material.

9. The intraocular lens of claim 1 wherein said lens optic portion is formed from a hydrogel material which is 18 percent by weight water.

10. The intraocular lens of claim 1 wherein said lens optic portion is formed from Poly(HEMA-co-HOHEXMA) and the iris fixation clamps are formed from polymethylmethacrylate.

11. The intraocular lens of claim 1 wherein said lens optic portion is formed from a material having a refractive index above 1.33.

12. The intraocular lens of claim 1 wherein said lens optic portion is formed from an acrylic material.

13. The intraocular lens of claim 1 wherein said lens optic portion is formed from a silicone material.

14. The intraocular lens of claim 1 wherein said haptic elements are dimensioned to be greater in a plane generally perpendicular to the eye's optical axis than that in a plane generally parallel to the eye's optical axis.

15. The intraocular lens of claim 1 wherein a glare reduction zone is formed adjacent to the outer peripheral edge of the optic portion.

16. The intraocular lens of claim 1 wherein one or more of said haptic elements includes a stiffening element having a greater resistance to bending in a plane generally perpendicular to an eye's optical axis than in a plane generally parallel to the eye's optical axis.

17. The intraocular lens of claim 1 wherein the haptic element includes a stiffening element formed from a material selected from the group consisting of polyimide, polyolefin, high-density polyester, nylon and metal.

18. A method of manufacturing the intraocular lens of claim 1 comprising:

forming a disk of one or more suitable materials, and machining said lens from said disk.

19. A method of manufacturing the intraocular lens of claim 1 comprising:

molding said lens of one or more suitable materials in a mold, and removing said lens from said mold.

20. A method of using the intraocular lens of claim 1 comprising:

creating an incision in a cornea of an eye, inserting said intraocular lens in an anterior chamber of said eye, and securing said intraocular lens within the anterior chamber.

* * * * *